(12) United States Patent
Zhang et al.

(10) Patent No.: US 7,905,013 B2
(45) Date of Patent: Mar. 15, 2011

(54) METHOD FOR FORMING AN IRIDIUM OXIDE (IROX) NANOWIRE NEURAL SENSOR ARRAY

(75) Inventors: Fengyan Zhang, Camas, WA (US); Bruce D. Ulrich, Beaverton, OR (US); Wei Gao, Vancouver, WA (US); Sheng Teng Hsu, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 953 days.

(21) Appl. No.: 11/809,959

(22) Filed: Jun. 4, 2007

(65) Prior Publication Data
US 2008/0299381 A1    Dec. 4, 2008

(51) Int. Cl.
*H01K 3/10*    (2006.01)

(52) U.S. Cl. ........... 29/852; 29/831; 29/832; 29/853; 29/854

(58) Field of Classification Search ............ 29/830, 29/831, 832, 852, 853, 854, 845, 837; 428/315.9; 427/126.5; 204/403.01; 977/811, 812, 932
See application file for complete search history.

(56) References Cited

U.S. PATENT DOCUMENTS

| | | | |
|---|---|---|---|
| 4,628,933 A | 12/1986 | Michelson | 128/419 R |
| 4,969,468 A | 11/1990 | Byers et al. | 128/642 |
| 5,109,844 A | 5/1992 | De Juan et al. | 128/419 R |
| 5,361,760 A | 11/1994 | Normann et al. | 128/642 |
| 5,865,839 A | 2/1999 | Doorish | 607/54 |
| 6,298,270 B1 | 10/2001 | Nisch et al. | 607/54 |
| 6,444,256 B1 * | 9/2002 | Musket et al. | 427/117 |
| 6,933,156 B2 * | 8/2005 | Wang et al. | 438/3 |
| 7,045,839 B2 * | 5/2006 | Song et al. | 257/295 |
| 2004/0133118 A1 * | 7/2004 | Llinas | 600/544 |

FOREIGN PATENT DOCUMENTS

JP    2008-29838    2/2008

* cited by examiner

*Primary Examiner* — Derris H Banks
*Assistant Examiner* — Tai Nguyen
(74) *Attorney, Agent, or Firm* — Law Office of Gerald Maliszewski; Gerald Maliszewski

(57) ABSTRACT

An iridium oxide (IrOx) nanowire neural sensor array and associated fabrication method are provided. The method provides a substrate with a conductive layer overlying the substrate, and a dielectric layer overlying the conductive layer. The substrate can be a material such as Si, $SiO_2$, quartz, glass, or polyimide, and the conductive layer is a material such as ITO, $SnO_2$, ZnO, $TiO_2$, doped ITO, doped $SnO_2$, doped ZnO, doped $TiO_2$, TiN, TaN, Au, Pt, or Ir. The dielectric layer is selectively wet etched, forming contact holes with sloped walls in the dielectric layer and exposing regions of the conductive layer. IrOx nanowire neural interfaces are grown from the exposed regions of the conductive layer. The IrOx nanowire neural interfaces each have a cross-section in a range of 0.5 to 10 micrometers, and may be shaped as a circle, rectangle, or oval.

10 Claims, 6 Drawing Sheets

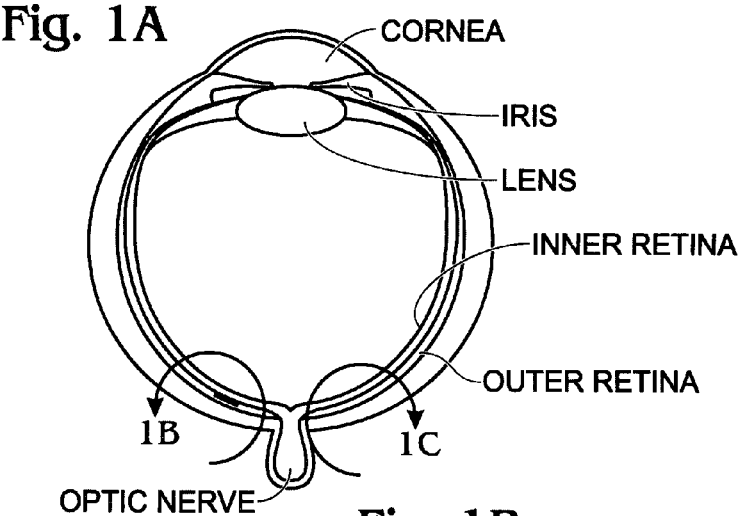
Fig. 1A
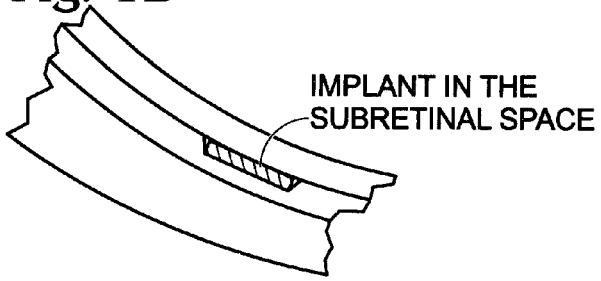
Fig. 1B SUBRETINAL
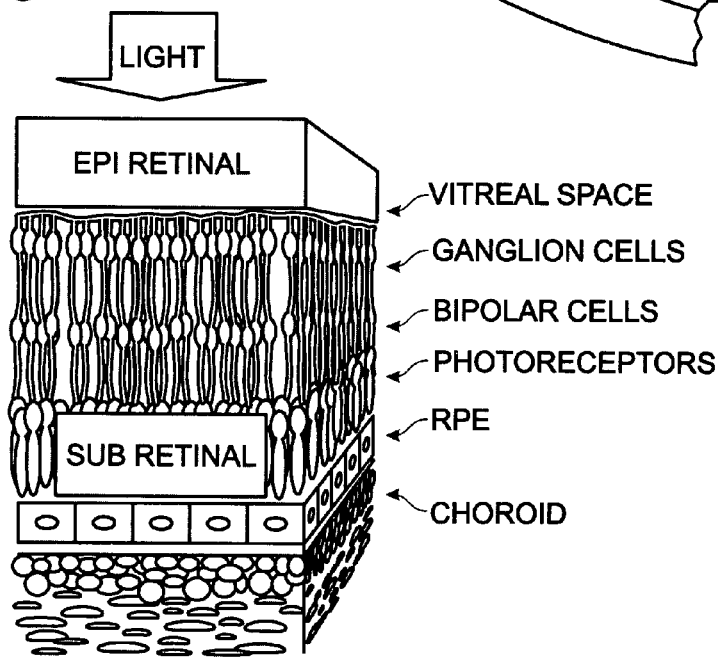
Fig. 1C EPIRETINAL (a) FLAT ELECTRODE (b) MICRO MACHINED ELECTRODE ARRAY

METHOD FOR FORMING AN IRIDIUM OXIDE (IROX) NANOWIRE NEURAL SENSOR ARRAY

BACKGROUND OF THE INVENTION

1. Field of the Invention

This invention generally relates to integrated circuit (IC) fabrication and, more particularly, to a fine resolution sensor with an iridium oxide nanowire neural interface.

2. Description of the Related Art

FIGS. 1A through 1C depict the placement of optical electrodes, using epiretinal and subretinal approaches (prior art). Studies show that blind patients with retinitis pigmentosa and masular degeneration can observe a visual percept induced by the direct electrical stimulation of the retina. Recently, retinal prosthesis development has progressed along two directions. The epiretinal approach places electrode in the vitreous fluid, attached to the surface of the retina, while the subretinal approach places electrodes on the outside of retina, wedged between the photoreceptors and the pigment epithelium. FIG. 1C shows the electrode positions for both type of retina prosthesis.

One major difficulty with the epiretinal approach is that the tissue has a very high resistance to electrical stimulation. This high electrical resistance is due to the fact that the retinal is covered by the inner limiting membrane, similar to the blood-brain barrier, and it is impermeable to many types of ions. Since electrical stimulation depends on electrical current building an electrical field across the target nerve cell, a high-resistance barrier in the stimulation pathway prevents current passage. Thus, current is diverted away to other, lower-resistance tissues. To compensate for this loss, the epiretinal approach requires a much larger charge at the electrode surface, to achieve the same stimulation level on the target tissue as a conventionally functioning eye. In human trials, a net charge of ~1 uC (micro-Coulomb) is required for the epiretinal approach, a very high charge for neural stimulation, when compared to 50 nC, which is the level typically required for central nervous system stimulation and subretinal stimulation.

One way to overcome the high-impedance barrier of the epiretinal approach is to penetrate the inner limiting membrane. Arrays of sharp electrodes have been fabricated from silicon and have been used for this purpose. Recently, new techniques promise nano-scale piecing wire electrodes, which can be formed by electrodeposition on a glass substrate contoured to fit the retina.

The subretinal prosthesis avoids the high-impedance barrier problem, by installing electrodes behind the retina. The electrodes are also very close to the bipolar cells, allowing easy (low-charge) stimulation. Low thresholds in the range of 2.8 to 100 nC/cm$^2$ have been reported. However, 178 uC/cm$^2$ is a more realistic number. Subretinal prostheses requires that all components be fitted behind the retina, with the circuits integrated with the electrodes. Power is transferred into the eye via light, which in theory is received by integrated photovoltaic cells, to activate the circuitry. The power output needs to be strictly controlled, since heat dissipation is limited in the subretinal space, and overheating can easily damage the retina.

One technical challenge is the trade-off between electrode density and stimulation charge. Although the total charge injection required to elicit a visual percept is fixed, the maximum charge an electrode can deliver is limited by its surface area. Surpassing this charge density threshold generates undesirable and irreversible electrochemical reactions. In order to elicit a visual percept, the charge density requirement dictates that the electrode must have a total surface area of 1 mm$^2$. When considering the limited area of the retinal implant, this constraint translates into a resolution of 5×5 (25 pixels). However, a visual resolution of at least 25×25 pixels (625 pixels) is desired for recovery of functional sight.

To inject more charge without hydrolysis, an electrode made from a material with a higher injection limit can be used, such as iridium oxide (IrOx). As a biocompatible electrode material, IrOx has advantages over Au and Pt and Pt. Au quickly dissolves when a high potential is applied. Pt has the longest history as an electrode material and is the best characterized. Compared to IrOx, the performance of Pt is limited because it cannot sustain as much reversible faradic charge, and it catalyzes water electrolysis at low voltages, limiting its charge-injection capability. Compared to Pt, an IrOx electrode can inject much more charge for a given voltage swing, by cycling iridium through many oxidation states. Because iridium can exist in many valence states with an insignificant change in atomic size, an iridium electrode can cycle from metallic form (Ir) to higher oxidized form (IrO$_4$) reversibly, allowing it to have a high charge-injection limit of 1 mC/cm$^2$. Using cyclic voltammetry with scan rates of 0.06V/s or slower, a charge injection of >25 mC/cm$^2$ can often be obtained. This behavior is attributed to IrOx porous structure, which requires ionic species to diffuse into deep recessed regions to access the full surface area, as well as due to its many oxidation states, requiring the completion of one state change before proceeding to the next reaction. IrOx is especially ideal for applications with slower stimulation waveforms. For neural stimulation, a current pulse longer than 200 us can be employed. Furthermore, IrOx needs to be biased so that its oxidation state is between Ir3+ and Ir4+ to prevent dissolution that occurs at metallic or higher oxidation states. However, because it relies heavily on faradic reactions, IrOx is slower in delivering current.

A second approach to increasing electrode charge-injection involves enlarging the electrode surface area. The surface area of an electrode is a strong function of its geometry. The area of a solid post electrode can be increased by a factor of 10 easily if it is formed into an array of nanowires/tubes/rods.

FIG. 2 is a schematic diagram modeling the interface between an electrode and chemically active solution (prior art). Electrodes pass charge mainly through two mechanisms: faradic reactions and capacitive charging. Capacitive charging is the accumulation of charge at the interface between electrons in a metal electrode and ions adjacent to the electrode in a solution, and is represented by $C_E$. A faradic reaction is the transfer of electrons with ions in a solution by a redox reaction of metal species, and is represented by $R_E$. Both the capacitive and faradic components increase linearly with the electrode area because more charge can accumulate at the interface area and be transferred through chemical reactions by increasing the size of the electrode. This larger electrode can be modeled as having a smaller $R_E$ and bigger $C_E$, leading to an increased electrode current at a given potential. Pulses of either constant voltage or current can be used for electrical stimulation. Most frequently, pulses of constant current are used.

FIG. 3 is a partial cross-sectional view comparing a conventional flat electrode with an electrode array (prior art). Micro-machined neural-stimulating electrode array technology has also been researched. The micro-machined electrode has the advantage of providing additional surface area to decrease the current density, while increasing the electrode density and avoiding material corrosion. However, a key issue to be resolved is the fabrication of an electrode array that can conform to the concave shape of the foveal pit. For example, such as array would need to be formed on a flexible substrate (e.g., polyimide).

Another limitation associated with micromachining technology is size, as the individually machined electrodes cannot be made to a nano-size resolution. Even if a template of nano-sized structures could be micro-machined, plating an array of nanostructures, with a noble metal for example, in a sufficiently high aspect ratio is a big challenge. Micro-machined electrodes are normally formed from a thick film that is deposited using a physical vapor deposition (PVD) process or electrode plating. In either case, the resultant film, and micro-machined electrode post are typically a polycrystalline material.

Thus, research is ongoing in the investigation of nanowire-based neuron electrode arrays that can be used to promote the growth of subcellular highways via controlled electrical stimulation. Combined with quantum dots assisted imaging technology, these subcellular highways have potential in image transportation. Nanowire neuron arrays also have the potential to guide movement of drugs and other factors on subcellular highways. These applications may become important in therapy for conditions involving the defective transport of neurons and neurodegenerative disease, for example: Alzheimer's, Huntington's, Parkinson's, and acute brain injury.

Some challenges facing conventional neuron stimulating and recording electrodes are the lack of resolution in microfabricated structures. Poor resolution makes in impossible to stimulate subcellular regions of a single cell. This issue can be addressed with the use of grown nanostructures. Experiments with conductive carbon nanotubes (CNTs) have been conducted to test their effectiveness in neural guidance. However, CNTs are prone to bending and warping, and lack the robustness required for repeatable sensitive electrical measurements.

On the other hand, IrOx nanowire-based neuron electrode have a better surface to volume ratio, as compared to CNTs, as well as a high resolution stimulation, biocompatibility, and ability to grow on transparent conducting electrodes such as ITO, $SnO_2$, ZnO and $TiO_2$ with or without any doping.

Single-crystal $IrO_2$ nanowires/rods/tips have a much longer life than polycrystalline $IrO_2$, due to their higher chemical reaction resistance. Single-crystal IrOx nanostructures also have a higher conductance than polycrystalline $IrO_2$, so they can pass through current more efficiently. However, it is difficult to form single-crystal $IrO_2$ films using conventional PVD or electrode plating methods. $IrO_2$ nanostructures can be formed using a solution method, but these structures have a low mechanical strength and poor crystal quality. Vapor phase transport methods can also be used to form IrO2 nanostructures, but this process requires high substrate temperature, and it is not suitable for use with glass and polyimide substrates.

A technology that can grow free standing highly crystallized nanowires/tubes/rods array of $IrO_x$ on highly resolved areas of electrode would be useful in the fabrication of a neuron interface.

SUMMARY OF THE INVENTION

This application describes the fabrication process for an $IrO_X$ nanowire-based neuron electrode for stimulating and recording neuron activities, and for use in therapy for neurodegenerative diseases. Compared to micromachined neuron electrodes, $IrO_X$ nanowires have an improved surface to volume ratio, and a higher resolution—making them more capable of stimulating targeted areas. An IrOx nanowire sensor is biocompatibility and can be grown on a transparent conducting electrode for imaging applications.

Accordingly, a method is provided for forming an iridium oxide (IrOx) nanowire neural sensor array. The method provides a substrate with a conductive layer overlying the substrate, and a dielectric layer overlying the conductive layer. The substrate can be a material such as Si, $SiO_2$, quartz, glass, or polyimide, and the conductive layer is a material such as ITO, $SnO_2$, ZnO, $TiO_2$, doped ITO, doped $SnO_2$, doped ZnO, doped $TiO_2$, TiN, TaN, Au, Pt, or Ir. The dielectric layer is selectively wet etched, forming contact holes with sloped walls in the dielectric layer and exposing regions of the conductive layer. IrOx nanowire neural interfaces are grown from the exposed regions of the conductive layer. The IrOx nanowire neural interfaces each have a cross-section in a range of 0.5 to 10 micrometers, and may be shaped as a circle, rectangle, or oval.

In one aspect, the substrate is a substrate chip with edges, and prior to forming the dielectric layer, the conductive layer is etched to form electrodes, probe pads along the chip edges, and traces connecting the electrodes to the probe pads. Then, the step of forming contact holes in the dielectric layer may include forming a neural interface contact hole overlying each electrode and a probing pad contact hole, which overlies and exposes regions of each probing pad. IrOx nanowires can additionally be grown from the exposed regions of the probing pads.

Additional details of the above-described method and an IrOx nanowire neural sensor array are presented below.

BRIEF DESCRIPTION OF THE DRAWINGS

FIGS. 1A through 1C depict the placement of optical electrodes, using epiretinal and subretinal approaches (prior art).

DETAILED DESCRIPTION

Figure 2:
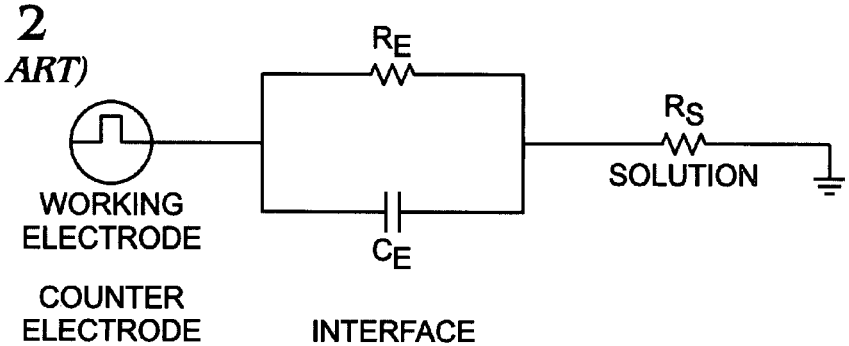
FIG. 2 is a schematic diagram modeling the interface between an electrode and chemically active solution (prior art).
Figure 3:
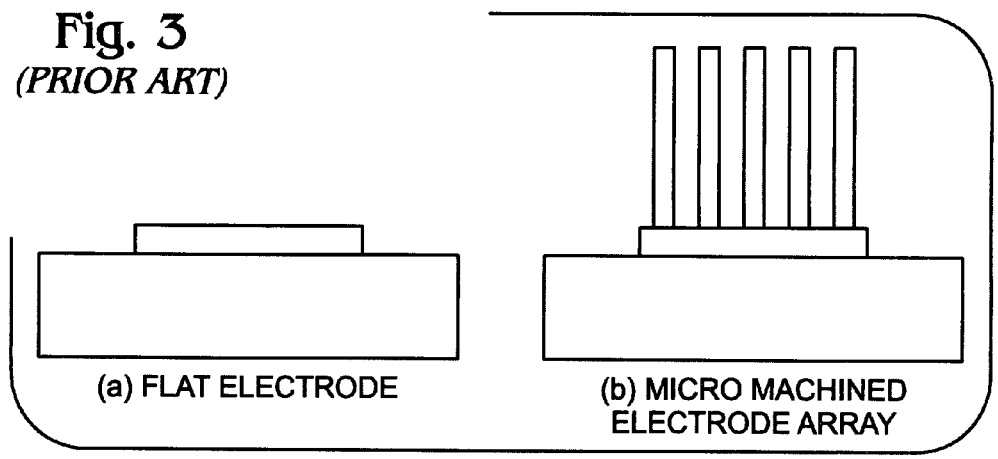
FIG. 3 is a partial cross-sectional view comparing a conventional flat electrode with an electrode array (prior art).
Figure 4:
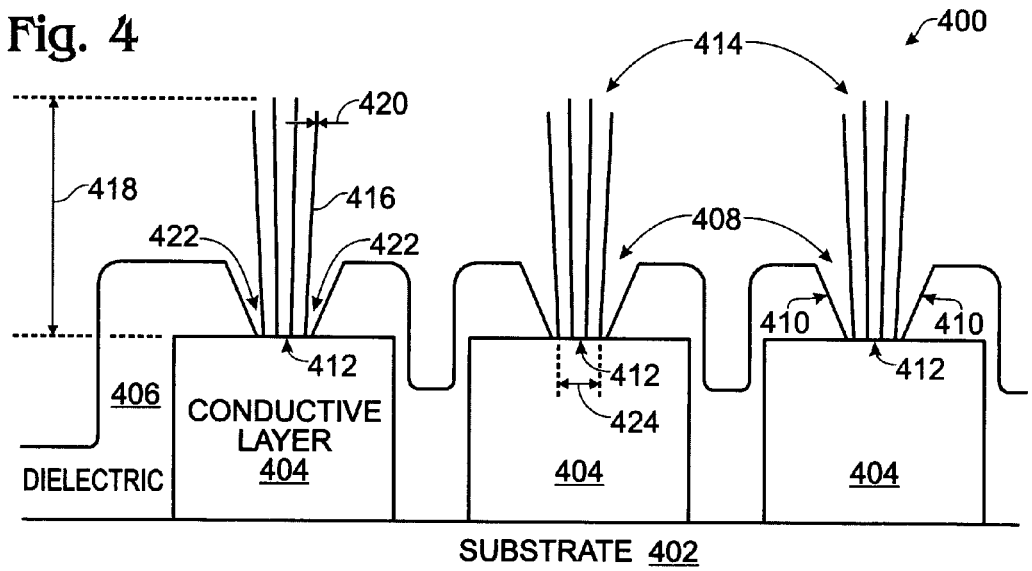
FIG. 4 is a partial cross-sectional view of an iridium oxide (IrOx) nanowire neural sensor array.

FIG. 4 is a partial cross-sectional view of an iridium oxide (IrOx) nanowire neural sensor array. The array 400 comprises a substrate 402 and a conductive layer 404 overlying the substrate 402. A dielectric layer 406 overlies the conductive layer 404. Contact holes 408 with sloped walls 410 are formed in the dielectric layer 406, exposing regions 412 of the conductive layer 404. IrOx nanowire neural interfaces 414 are shown, grown from the exposed regions 412 of the conductive layer 404. With respect to IrOx, typically x is ≦4. Although only 3 interfaces 414 are shown, the array is not limited to any particular number of interfaces. A nanowire may alternately be known as a nanostructure, nanorod, nanotip, or nanotube.

The average IrOx nanowire 416 has an aspect ratio in a range of about 1:1 to about 1:1000. As used herein, aspect ratio is defined as the ratio of the nanowire height 418, to the nanowire diameter or width 420 at proximal end 422 (base) attached to the conductive electrode 404. The IrOx nanowires have an average height 418 in the range of about 10 nanometers (nm) to about 10 micrometers ($\mu$m). The IrOx nanowires have an average proximal end diameter 420 in a range of about 1 nm to about 1 $\mu$m.

In one aspect, each IrOx nanowire neural interface 414 has a cross-section 424 in the range of 0.5 to 10 micrometers. If seen in a plan view from above (not shown), the nanowire neural interfaces would have a shape such as a rectangle, square, circle, or oval. However, the invention is not limited to any particular shape. Advantageously, the small cross-sectional area of the neural interface 414 permits an interface to made to biological features as small as individual cells. The conductive layer 404 is a material such as ITO, $SnO_2$, ZnO, $TiO_2$, doped ITO, doped $SnO_2$, doped ZnO, doped $TiO_2$, TiN, TaN, Au, Pt, or Ir. The substrate 402 may be a material such as Si, $SiO_2$, quartz, glass, or polyimide. The dielectric layer 406 may be an oxide or nitride material such as $SiO_2$ or SiN. However, the array 400 is not necessarily limited to the above-mentioned materials. These materials are mentioned as materials that can be readily adapted to conventional IC fabrication processes.

Figure 5A:
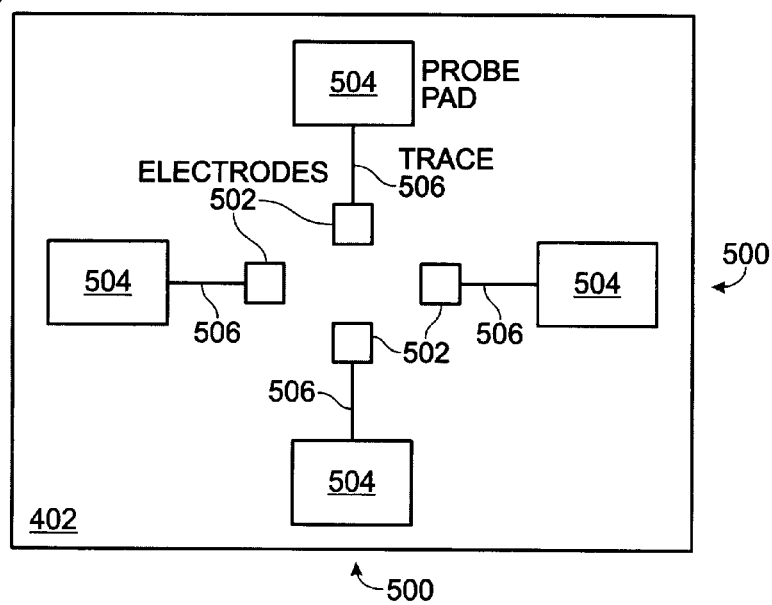
FIGS. 5A and 5B are plan and cross-sectional views, respectively, depicting a variation of the neural sensor array of FIG. 4.
Figure 5B:
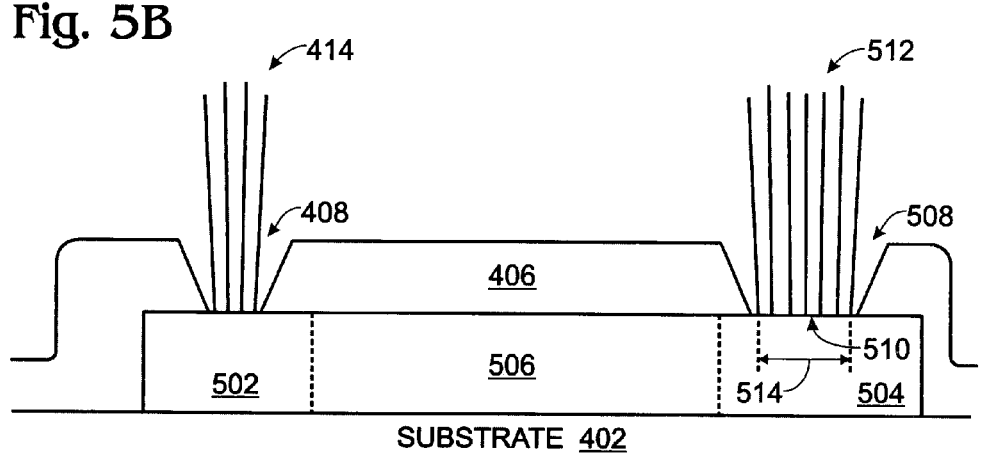

FIGS. 5A and 5B are plan and cross-sectional views, respectively, depicting a variation of the neural sensor array of FIG. 4. As seen in FIG. 5A, the substrate 402 is a chip with edges 500. Typically, the chip has an area in the range of 1 square millimeter ($mm^2$) to 100 $mm^2$. The conductive layer is formed into electrodes 502, probe pads 504 along the chip edges 500, and traces 506 connecting the electrodes 502 to the probe pads 504. Note: in this view the dielectric layer and IrOx nanowires are invisible.

As seen in FIG. 5B, the contact holes in the dielectric layer include the neural interface contact hole 408 overlying each electrode 502 and a probing pad contact hole 508 overlying and exposing regions 510 of each probing pad 504. An IrOx nanowire probe interface 512 is grown from the exposed regions 510 of each probing pad. In other aspects not shown, the probing pad 504 is left exposed without any IrOx nanowires grown from exposed region 510. The probing pad contact hole 508 typically has a diameter 514 in the range of 200 micrometers to 2 mm.

Figure 6A:
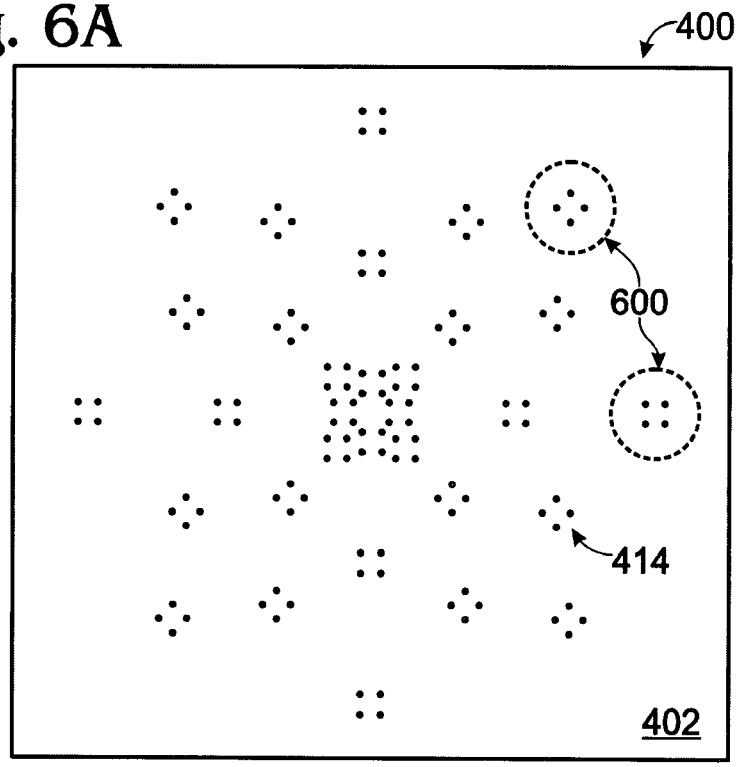
FIGS. 6A and 6B are plan views depicting other variations of the neural sensor array of FIG. 4.
Figure 6B:
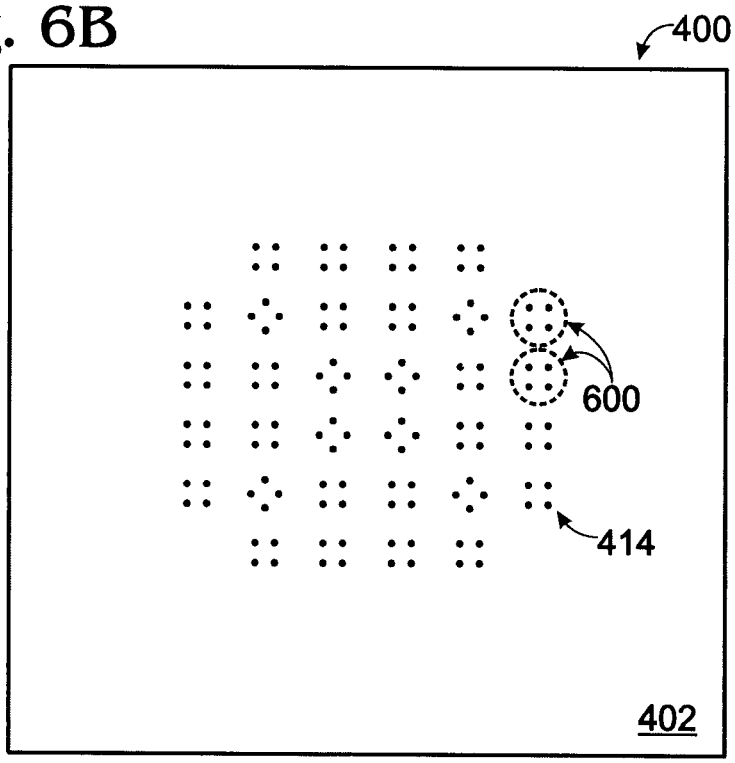

FIGS. 6A and 6B are plan views depicting other variations of the neural sensor array of FIG. 4. The IrOx nanowire neural interfaces form an array of neural interface clusters 600 in a center region of the substrate 402, where each cluster includes between 2 and 12 electrodes (neural interfaces). As shown, each dot represents a neural interface, and all the neural interface clusters in these examples include 4 neural interfaces. Each cluster 600 has a cluster diameter in the range of 5 to 50 micrometers ($\mu$m). The cluster diameter is the distance between the furthest neural interfaces in a cluster. Note: the cluster diameters and number of neural interfaces per cluster need not necessarily be uniform. As shown in FIGS. 6A and 6B, the cluster diameters are approximately 10 $\mu$m. The number of clusters on the substrate is typically in the range between 2 and 100, and they can be arranged in a pattern such as a circle, rectangle, or a grid. There are 32 clusters in each of the examples shown in FIGS. 6A and 6B. The cluster pattern of FIG. 6A may be referred to as a circular pattern, while the pattern of FIG. 6A is rectangular.

The distance between clusters on the substrate may be uniform or varied, and may be measured from the substrate center or from adjacent clusters. In FIG. 6A, the distance between clusters may be measured as a function of the relative position of the cluster from the substrate center. In the first "ring" of clusters, the distance from center is approximately 25 $\mu$m, in the second ring the distance is 50 $\mu$m, in the third ring the distance is 75 $\mu$m, and in the fourth ring the distance is 100 $\mu$m. In FIG. 6B, the distance between adjacent clusters is 50 $\mu$m.

Functional Description

Figure 7A:
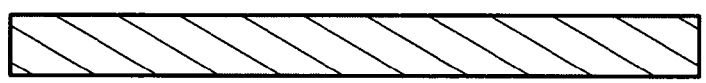
FIGS. 7A through 7E are partial cross-sectional views depicting steps in the fabrication of an IrOx nanowire neural sensor.
Figure 7B:
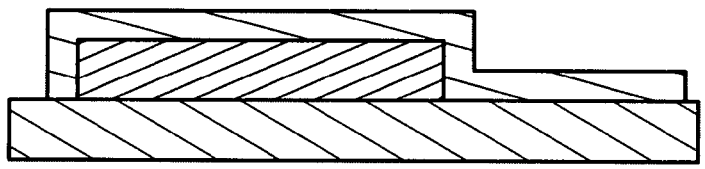

FIGS. 7A through 7E are partial cross-sectional views depicting steps in the fabrication of an IrOx nanowire neural sensor. A substrate is provided, as shown in FIG. 7A. A conductive layer such as Pt, Au, TiN or ITO is deposited on Si, $SiO_2$, quartz, or plastic wafers (see FIG. 7B). If ITO is used, an optional annealing process can be performed in oxygen at 200-600° C. for 10 to 3600 seconds to improve the transparency of the ITO film. Then, the conductive layer is patterned using a wet or dry etching process. In case of ITO, wet etching may be performed using an HCl based solution. After patterning the conductive layer, a dielectric layer such as $SiO_2$ or SiN is deposited on the wafer to passivate the conductive lines.

Figure 7C:
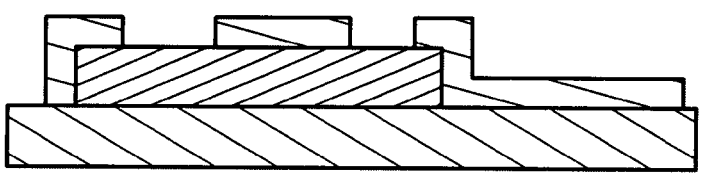
Figure 7D:
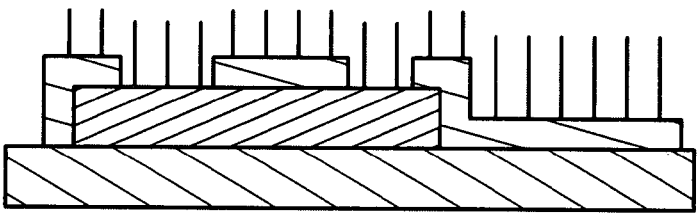

In FIG. 7C, contact holes to the conductive layer are etched out using either dry or wet etching process. In case of $SiO_2$ or undensified SiN dielectric, an HF based solution can be used to open up the contact holes. After etching, the wafer is transferred to $IrO_2$ chamber to grow $IrO_2$ or IrOx nanowires, see FIG. 7D. Normally, the $IrO_2$ (IrOx) nanowires are grown on both the exposed conductive surface and also on dielectric surface.

Figure 7E:
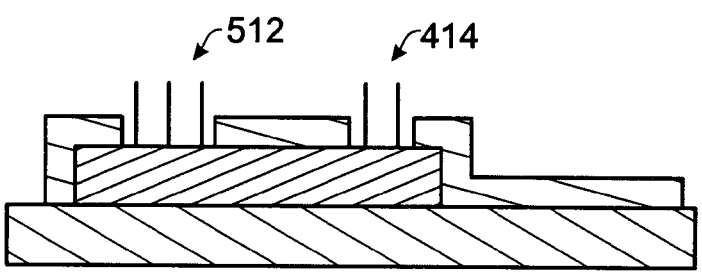

In FIG. 7E, a second wet etching process is used to stripe the field $IrO_2$ nanowires (on the dielectric), leaving the $IrO_2$ nanowires in the contact holes in place. If $SiO_2$ or undensified SiN is used, an HF based solution also works well to stripe the field $IrO_2$ nanowires. In this second etching step, the dielectric layer is partially striped away, leaving a sufficient thickness to passivate the conductive layer. FIG. 7E depicts a neural interface 414 and a probe interface 512 connected by a conductive layer trace. Note: the figure is not drawn to scale.

One advantages of using a nanowire in a neural interface is that such as array can provide multiple electrical contacts at the cellular level, for electronically discriminating amongst individual cells or small groups of cells within a tissue or organ. Such an array can direct electrical signals to or from individual cells, or small groups of cells within such tissue or organ, especially neural tissues and organs. Neurologists have long sought electrode devices that can establish stable electrical contact with a large number of individual nerve fibers within a nerve. The ideal electrode device can be adapted to the anatomy of the nerve so that it can penetrate the nerve in a nondestructive fashion, in order to form focused individual electrical contacts with a very large number of individual nerve fibers. In order to make electrical contact with individual nerve fibers within a nerve, the use of a nanowire array is a good design choice.

$IrO_2$ and IrOx nanostructures have been successfully grown on Si, polysilicon, glass, and ITO-coated polyimide flexible substrates, to name a few materials. Selective deposition can be obtained using refractory metal nano-particles, such as Ti, Ni, Au, etc. The growth length, density, and vertical orientation can be controlled by temperature, pressure, flow, substrates, and time.

Figure 8:
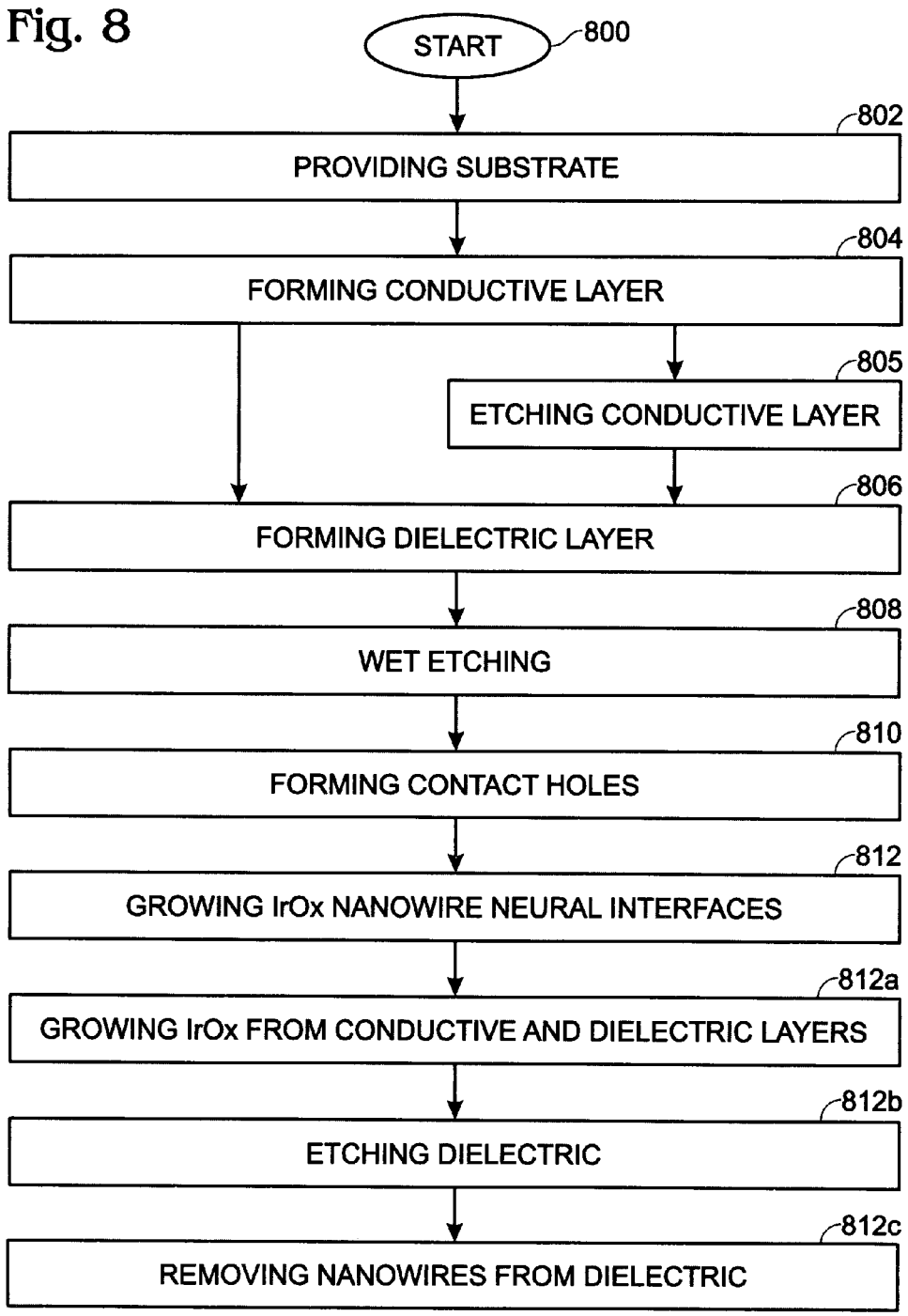
FIG. 8 is a flowchart illustrating a method forming an IrOx nanowire neural sensor array.

FIG. 8 is a flowchart illustrating a method forming an IrOx nanowire neural sensor array. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. The method starts at Step 800.

Step 802 provides a substrate such as Si, SiO$_2$, quartz, glass, or polyimide. Step 804 forms a conductive layer overlying the substrate, from a material such as ITO, SnO$_2$, ZnO, TiO$_2$, doped ITO, doped SnO$_2$, doped ZnO, doped TiO$_2$, TiN, TaN, Au, Pt, or Ir. Step 806 forms a dielectric layer overlying the conductive layer from an oxide or nitride material such as SiO$_2$ and SiN. Step 808 selectively wet etches the dielectric layer. Step 810 forms contact holes with sloped walls in the dielectric layer, exposing regions of the conductive layer. Step 812 grows IrOx nanowire neural interfaces from the exposed regions of the conductive layer.

When growing IrOx nanowires from a small hole, a shadowing effect associated with the hole or via walls inhibits the growth of the nanowires. Therefore, a wet etching process is used which forms a sloped, as opposed to vertical wall structure, where the narrow aperture of the hole is adjacent (overlying) the conductive layer. Since the wall of the contact hole is sloped, the shadowing effect is reduced, enabling the growth of nanowires in aperture diameters as small as 0.5 um. Typically, the growth of the IrOx nanowire neural interface in Step 812 includes forming each neural interface with a cross-section in the range of 0.5 to 10 micrometers, with a shape such as a circle, rectangle, or oval.

In another aspect, growing IrOx nanowire neural interfaces in Step 812 includes substeps. Step 812a grows IrOx nanowires from the exposed regions of conductive layer and from a top surface of the dielectric layer. Step 812b selectively etches the dielectric layer, and Step 812c removes the IrOx nanowires from the dielectric layer top surface.

In one aspect, providing the substrate in Step 802 includes providing a substrate chip with edges. Then prior to forming the dielectric layer in Step 806, Step 805 etches the conductive layer to form electrodes, probe pads along the chip edges, and traces connecting the electrodes to the probe pads. Forming contact holes in the dielectric layer in Step 810 includes forming a neural interface contact hole overlying each electrode and a probing pad contact hole overlying and exposing regions of each probing pad. Step 812 may additionally grow IrOx nanowires from the exposed regions of the probing pads.

In another aspect, Step 802 provides a substrate chip having an area in the range of 1 mm$^2$ to 100 mm$^2$. Etching the conductive layer to form electrodes in Step 805 includes forming an array of electrode clusters in a center region of the substrate, where each cluster includes between 2 and 12 electrodes. Each cluster has a diameter in the range of 5 to 50 micrometers. The number of clusters on a chip is in the range of 2 and 100, and the clusters are arranged in a pattern such as a circle, rectangle, or a grid.

Additional details of the IrOx nanowire fabrication process can be found in the following related pending applications:

OPTICAL DEVICE WITH IrOx NANOSTRUCTURE ELECTRODE NEURAL INTERFACE, invented by Zhang et al, Ser. No. 11/496,157, filed Jul. 31, 2006;

IRIDIUM OXIDE NANOTUBES AND METHOD FOR FORMING SAME, invented by Zhang et al., Ser. No. 10/971,280, filed Oct. 21, 2004; and, IRIDIUM OXIDE NANOWIRE AND METHOD FOR FORMING SAME, invented by Zhang et al., Ser. No. 10/971,330, filed Oct. 21, 2004. The three above-mentioned applications are incorporated herein by reference.

An IrOx nanowire neural sensor array and corresponding fabrication processes have been provided. Examples of specific materials, process steps, and structures have been presented to illustrate the invention. However, the invention is not limited to merely these examples. Other variations and embodiments of the invention will occur to those skilled in the art.

We claim:

1. A method for forming an iridium oxide (IrOx) nanowire neural sensor array, the method comprising:
   providing a substrate;
   forming a conductive layer overlying the substrate;
   forming a dielectric layer overlying the conductive layer;
   selectively wet etching the dielectric layer;
   forming contact holes in the dielectric layer and exposing regions of the conductive layer; and,
   growing iridium oxide IrOx nanowire neural interfaces from the exposed regions of the conductive layer.

2. The method of claim 1 wherein growing the IrOx nanowire neural interfaces includes forming each neural interface with a cross-section in a range of 0.5 to 10 micrometers and a shape selected from a group consisting of a circle, rectangle, and oval.

3. The method of claim 1 wherein forming the conductive layer overlying the substrate includes forming a conductive layer from a material selected from a group consisting of ITO, SnO$_2$, ZnO, TiO$_2$, doped ITO, doped SnO$_2$, doped ZnO, doped TiO$_2$, TiN, TaN, Au, Pt, and Ir.

4. The method of claim 1 wherein providing the substrate includes providing a substrate material selected from a group consisting of Si, SiO$_2$, quartz, glass, and polyimide.

5. The method of claim 1 wherein providing the substrate includes providing a substrate chip with edges;
   the method further comprising:
   prior to forming the dielectric layer, etching the conductive layer to form electrodes, probe pads along the chip edges, and traces connecting the electrodes to the probe pads.

6. The method of claim 5 wherein forming contact holes in the dielectric layer includes forming a neural interface contact hole overlying each electrode and a probing pad contact hole overlying and exposing regions of each probing pad; and,
   wherein growing iridium oxide IrOx nanowire neural interfaces additionally includes growing iridium oxide IrOx nanowires from the exposed regions of the probing pads.

7. The method of claim 5 wherein growing iridium oxide IrOx nanowire neural interfaces includes:
   growing iridium oxide IrOx nanowires from the exposed regions of conductive layer and from a top surface of the dielectric layer;
   selectively etching the dielectric layer; and,
   removing the iridium oxide IrOx nanowires from the dielectric layer top surface.

8. The method of claim 5 wherein providing the substrate chip includes providing a chip having an area in the range of 1 square millimeter (mm$^2$) to 100 mm$^2$; and,
   wherein etching the conductive layer to form electrodes includes forming an array of electrode clusters in a center region of the substrate, where each cluster includes between 2 and 12 electrodes, located within a cluster diameter in the range of 5 to 50 micrometers, where the number of clusters on the chip is in a range between 2 and 100, and the clusters are arranged in a pattern selected from a group consisting of a circle, rectangle, and a grid.

9. The method of claim 1 wherein forming the dielectric layer includes forming a dielectric layer from a material selected from a group consisting of $SiO_2$ and SiN.

10. The method of claim 1 wherein forming contact holes in the dielectric layer includes forming contact holes with sloped walls in the dielectric layer.

\* \* \* \* \*